(12) United States Patent
Birecki et al.

(10) Patent No.: US 9,003,972 B2
(45) Date of Patent: Apr. 14, 2015

(54) REFLECTION DENSITOMETER

(75) Inventors: Henryk Birecki, Palo Alto, CA (US); William D. Holland, Palo Alto, CA (US); Omer Gila, Cupertino, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 603 days.

(21) Appl. No.: 13/259,102

(22) PCT Filed: Jan. 7, 2010

(86) PCT No.: PCT/US2010/020325
§ 371 (c)(1),
(2), (4) Date: Sep. 22, 2011

(87) PCT Pub. No.: WO2011/084158
PCT Pub. Date: Jul. 14, 2011

(65) Prior Publication Data
US 2012/0012018 A1    Jan. 19, 2012

(51) Int. Cl.
*B41F 33/00* (2006.01)
*G01N 33/32* (2006.01)

(52) U.S. Cl.
CPC ............ *G01N 33/32* (2013.01); *B41F 33/0036* (2013.01); *Y10S 101/45* (2013.01)

(58) Field of Classification Search
CPC ............ B41F 33/0045; B41F 33/0054; B41F 33/0036; B41F 33/0063; B41P 2233/51; B41P 2233/11; G01J 1/42; G01J 1/04; G01J 1/4257; G01J 1/4214
USPC ........... 101/DIG. 45, 484, 483, 480; 356/218, 356/224
See application file for complete search history.

(56) References Cited

U.S. PATENT DOCUMENTS

| 3,756,725 | A  | * | 9/1973  | Manring .................... 356/425 |
| 3,970,393 | A  | * | 7/1976  | Krygeris et al. ............ 356/425 |
| 5,224,421 | A  | * | 7/1993  | Doherty .................... 101/211 |
| 5,724,259 | A  | * | 3/1998  | Seymour et al. ............ 382/199 |
| 6,147,698 | A  |   | 11/2000 | Zable et al. |
| 7,077,064 | B1 | * | 7/2006  | Rich ........................ 101/484 |
| 7,502,116 | B2 | * | 3/2009  | Gila et al. ................. 356/443 |
| 2003/0058295 | A1 |   | 3/2003 | Heiles et al. |
| 2005/0052654 | A1 | * | 3/2005 | Gila et al. ................. 356/443 |
| 2007/0086071 | A1 | * | 4/2007 | Gila et al. ................. 358/518 |

FOREIGN PATENT DOCUMENTS

| CN | 101259783     | 9/2008  |
| CN | 201373833     | 12/2009 |
| EP | 1515134       | 3/2005  |
| GB | 1338464       | 11/1973 |
| KR | 1019980063960 | 10/1998 |

OTHER PUBLICATIONS

International Searching Authority, International Search Report and The Written Opinion, 10 pages, Sep. 2010.

* cited by examiner

*Primary Examiner* — Daniel J Colilla
*Assistant Examiner* — Leo T Hinze
(74) *Attorney, Agent, or Firm* — Hewlett-Packard Development Company, L.P.

(57) ABSTRACT

A method for determining optical density is disclosed. A first measurement is taken on a white area of a substrate (402). A second measurement is taken on an area of the substrate printed with ink (404). A relative optical density of the ink is determined using the first and second measurements (406).

13 Claims, 2 Drawing Sheets

REFLECTION DENSITOMETER

CROSS-REFERENCE TO RELATED APPLICATION

This application is a national stage application under 35 U.S.C. §371 of PCT/US2010/020325, filed Jan. 7, 2010.

BACKGROUND

Consistent color reproduction using a digital printer requires measurement and control of the densities for each ink used on a printed page. Typically the densities of the inks are measured using reflection densitometers. Commercial densitometers may range in price from $500 up to $2,000. One reason these commercial densitometers are so costly is that they typically meet the International Standards Organization (ISO) standards for measuring optical density. Unfortunately, including a commercial densitometer with each printer may not be economically viable.

DETAILED DESCRIPTION

FIGS. 1-4, and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figures 1A, 1B:
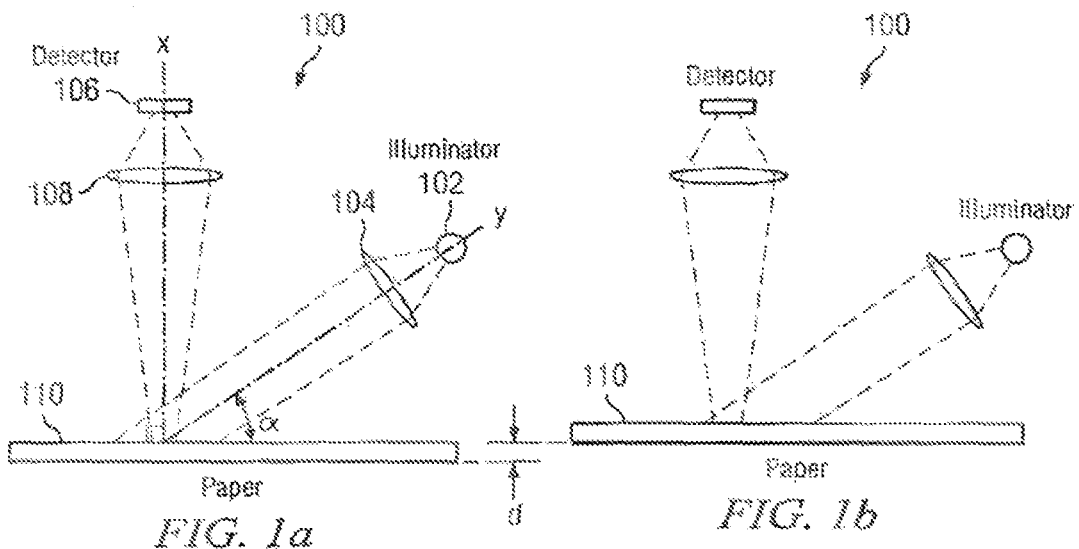
FIG. 1a is a color densitometer 100 in an example embodiment of the invention.
FIG. 1b is the color densitometer 100 with a different paper height, in an example embodiment of the invention.

FIG. 1a is a color densitometer 100 in an example embodiment of the invention. Color densitometer 100 comprises illumination source 102, illumination optics 104, detector 106, and detector optics 108. Illumination source 102 may be any type of light source, for example a light emitting diode (LED) Illumination source 102 may emit light over a broad or narrow wavelength band. Illumination optics 104 may be one or more lenses configured to create a focused beam of light from illumination source 102. Illumination optics 104 is configured to direct the focused beam of light onto a target, for example paper 110. Detector 106 may be any type of device that responds to the presence of light, for example a charged coupled device (CCD) or a photomultiplier. Detector optics 108 may be one or more lenses configured to direct light from the target onto detector 106. Detector optics is configured to collect light from the area of the target illuminated by the focused beam of light from illumination source 102.

In one example embodiment of the invention, the focused beam of light from illumination source 102 forms optical axis Y. Optical axis Y makes an angle α with paper 110. Angle α is typically set at 45 degrees. Detector and detector optics form an optical axis X. Optical axis X is typically set at 90 degrees to the surface of paper 110. FIG. 1b is color densitometer 100 with the height of the target paper 110 changed by distance d. Because optical axis Y makes a 45 degree angle with paper 110, shifts in paper height d, cause shifts in the position of the illumination at the location where detector 106 measures the optical density of the paper 110. The shift in the position of the illumination beam relative to the target area may change the illumination intensity and cause inaccuracies in the measured optical density.

Figure 2:
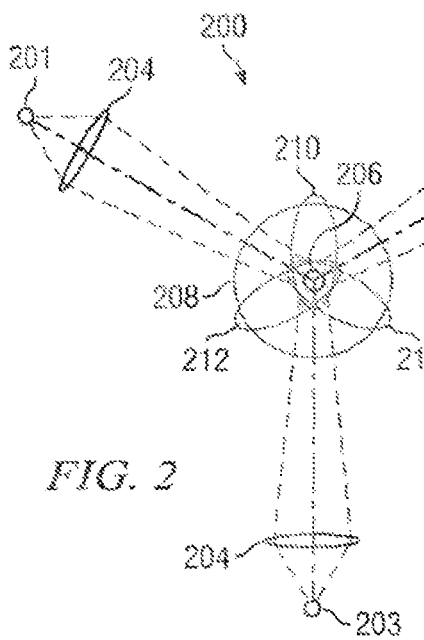
FIG. 2 is a top view of color densitometer 200 in an example embodiment of the invention.

In some example embodiments of the invention, there may be multiple illumination sources positioned around detector and detector optics. FIG. 2 is a top view of color densitometer 200 in an example embodiment of the invention. Color densitometer 200 comprises illumination sources 201, 202, 203, illumination optics 204, detector 206, and detector optics 208. The three illumination sources 201, 202, 203 are spaced equally around detector 206. Each illumination source (201, 202, and 203) has illumination optics 204 that forms a focused beam of light directed to a target location underneath detector 206 and detector optics 208.

The three sets of illumination sources and illumination optics form three focused beams of light. The focused beams of light from illumination sources 201, 202, and 203 forms three optical axes that make an angle α with the target. Angle α is typically set at 45 degrees. Detector and detector optics form an optical axis that is typically set at 90 degrees to the surface of the target (coining out of the paper in FIG. 2). In one example embodiment of the invention, the three illumination sources produce three different colors of light, for example red, green and blue. The three beams of light from the three illumination sources create three overlapping areas of illumination 210, 212, and 214 at the target area. Where the three illumination areas overlap, the target area is effectively illuminated by white light. In other example embodiments of the invention, the optical paths of the illumination optics and/or the detector optics may be folded or bent to reduce the physical size of the color densitometer 200. The number and color of the illumination sources may also be varied, for example four illumination sources that produce red, green, blue and orange light.

In operation, color densitometer (100, 200) measures the diffuse light from a target area on the page. The target area on the page may have one or more colors of ink printed on the page. The intensity measured by the densitometer is made up of two components, the system geometry, and the intensity modulation caused by the ink as shown by Equation 1.

$$\text{Measured intensity}=\text{intensity(geometry)}*\text{Intensity-Modulation(ink)}. \quad \text{(Equation 1)}$$

Equation 1 shows that if two measurements are made using the same color densitometer, the system geometry component in the measured signal may be eliminated. The two measurements are: a patch with ink printed on a sample page and a patch with no ink printed on the sample page. The signal from the first measurement is divided by the signal from the second measurement as shown below in equation 2. By dividing the two measurements, the intensity(geometry) term is canceled out of the equation.

$$\text{Relative Intensity}=*\text{IntensityModulation(ink)}/*\text{IntensityModulation(no ink)} \quad \text{(Equation 2)}$$

$$\text{Relative Intensity}=\text{IntensityModulation(ink)}/\text{IntensityModulation(no ink)} \quad \text{(Equation 2)}$$

Equation 2 is the Relative Intensity of the ink printed on the page. Changes in the reflected intensity are usually expressed in terms of absolute optical density (OD) which is expressed as $\log_{10}$(Intensity/Illumination intensity). To provide interchangeability and interoperability between densitometers, ISO standards for reflection density measurements[2,3,4] have been defined: 1. ISO standard 5-1 1984: *Photography—Density Measurements—Part 1: Terms, symbols and notations*. 2. ISO standard 5-3 1995: *Photography—Density Measurements—Part 3: Spectral conditions*. 3. ISO standard 5-4 1995: *Photography—Density Measurements—Part 4: Geometric conditions for reflection density*. Herein we refer to Relative OD as being $\log_{10}$(Relative Intensity).

The variation in measurements due to changes in the height of the paper with respect to the detector has been eliminated from the relative OD. By using the relative OD, the tolerance in the height between the detector and the surface of the printed paper may be relaxed. The relative OD will be determined during operation by taking two measurements. First a white area on the sample page (with no ink printed on the page) will be measured. Then a second area on the page Where ink has been printed will be measured. The relative intensity or relative OD is the second intensity divided by the first intensity. In one example embodiment of the invention, the printed and non-printed patches will be adjacent to each other. When the two patches are adjacent, any difference in height between the two measurements will be minimized.

Figure 3:
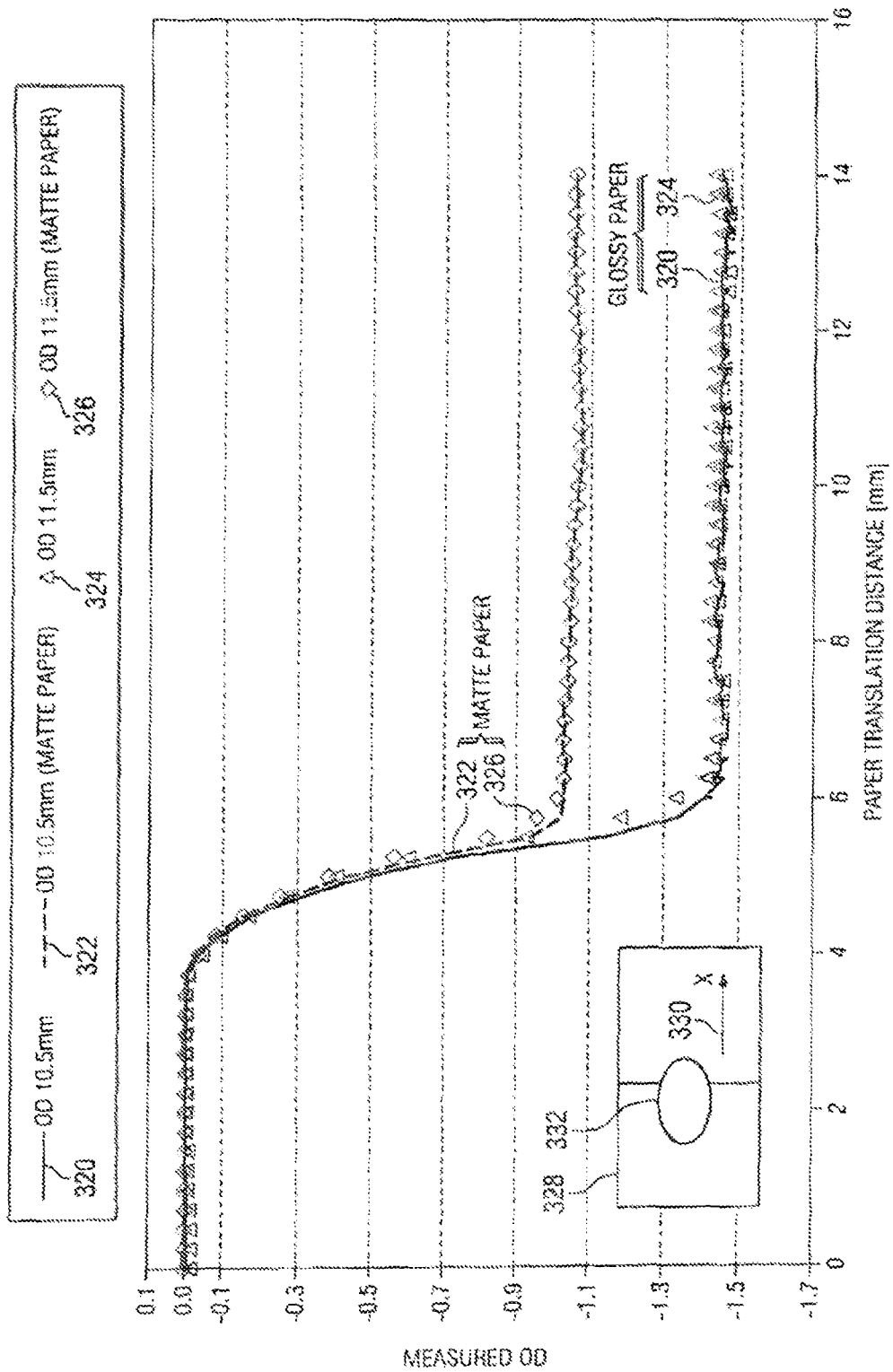
FIG. 3 is a graph showing the relative intensity (using equation 2) of the same test area on a printed page using the same densitometer with two different heights between the page and the detector in an example embodiment of the invention.

FIG. 3 is a graph showing the relative OD (using equation 2) of the same test area on a printed page using the same densitometer with two different heights between the page and the detector in an example embodiment of the invention. The intensity measurements in FIG. 3 where taken as the measurement area 332 from a densitometer was moved across two patches (328 and 330) on a sample page. The first patch 328 is a white area on the page With no ink printed on the page. The second patch 330 is an area on the page colored black by ink printed on the page. The X-axis of the graph is a measurement of the distance the densitometer was moved across the two patches. The Y-axis is the relative OD measured by the densitometer.

The measurements in FIG. 3 were taken in two steps, first a measurement of only patch 328 was done to determine IntensityModulation(no ink) for use in equation 2. Then measurements where taken as the measurement area 332 was moved from patch 328 onto patch 330 using equation 2 loaded with the value for IntensityModulation(no ink). When the measurement area 332 of the densitometer is completely over the white area, the measured relative OD is equal to zero. As the measurement area 332 of the densitometer moves onto patch 330, the measured relative OD decreases. Once the measurement area 332 of the densitometer is completely over patch 330, the measured relative OD flattens out at a constant value.

Line 320 is the relative OD measured from glossy paper, with a height of 10.5 mm between the paper and the detector. Line 324 is the relative OD measured from glossy paper with a height of 11.5 dim between the paper and the detector. Even though the distance between the paper and the detector is different between line 320 and 324, the measured relative OD is the same. This shows that the height sensitivity has been eliminated.

Line 322 is the relative OD measured from matte paper with a height of 10.5 mm between the paper and the detector. Line 326 is the relative OD measured from matte paper with a height of 11.5 mm between the paper and the detector. Even though the distance between the paper and the detector is different between line 322 and 326, the measured relative OD is the same. This shows that the height sensitivity has been eliminated.

The measured relative intensity, or relative optical density, can be converted to an absolute optical density of the printed patch by adding the absolute optical density (OD) of the paper to the measured relative OD (Absolute OD Patch=relative OD patch+absolute OD substrate). The absolute OD of the paper is a paper property and does not change during printing. The absolute OD of the paper can be looked up in a table, measured externally (i.e. not during printing), or measured during the printing process.

In one example embodiment of the invention, the densitometer may be used to determine the absolute OD of a non-printed area on the sample page during the printing process. The absolute OD of the non-printed area or patch may be determined using one of two methods. In the first method, the illumination source in the color densitometer having the least sensitivity to height variations is used to measure the non-primed patch. This measurement is used as the absolute OD of the non-printed paper. The illumination source in the color densitometer having the least sensitivity to height variations can be determined during the manufacturing process for the color densitometer.

In the second method, the height sensitivity of each of the illumination sources in the color densitometer are determined and saved during the manufacturing process. During operations, the OD of the white area on the page is measured using each illumination source in the color densitometer. Because a color densitometer typically has at least three illumination sources, there are two unknowns (the height between the detector and the paper and the absolute OD of the paper) and three equations (the measured sensitivity of each of the illumination sources to variations in the height between the paper and the detector), therefore the absolute OD of the paper can be determined.

The two methods above assume that the paper is white, i.e the absolute OD for each color channel is the same. This may not be true for all substrates. For colored substrates the table lookup from off press measurement still applies.

Figure 4:
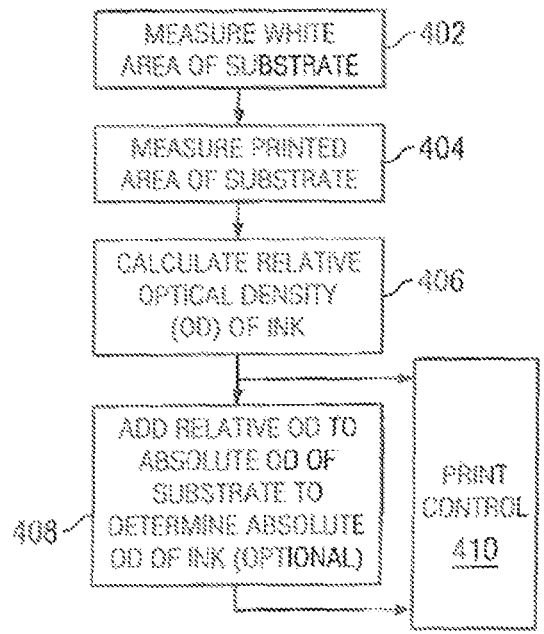
FIG. 4 is a flow chart for a method of controlling the OD of ink in a printing process, in an example embodiment of the invention.

FIG. 4 is a flow chart for a method of controlling the OD of ink in a printing process, in an example embodiment of the invention. The method starts at step 402 where a white area of the substrate is measured. A white area is an area on the substrate without any ink. Depending on the type of substrate, the white area may not actually be the color white. At step 404 an area on the substrate that has been printed with ink is measured. In some example embodiments of the invention, the two areas may be adjacent. At step 406 the relative optical density (OD) of the ink is calculated. The relative OD of the ink is calculated using equation 2. The relative OD of the ink may be used to control the printing process. Optionally, the absolute OD of the ink may be determined at step 408. The absolute OD of the ink may be used to control the printing process. The absolute OD of the ink may be determined using a known absolute OD of the substrate or a measured absolute OD of the substrate. The substrate may be any type of material that can receive ink, for example sheets or rolls of paper, cardboard, cloth, wood, metal, or the like.

A color densitometer (as described above) may be used to implement the method for controlling the OD of ink in a printing process as described in FIG. 4. One or more color densitometers may be mounted on the printer, and used to measure and control the OD of the ink during the printing process. Because the height sensitivity in the measurements from the color densitometer has been minimized, the color densitometer may not need to meet the ISO standards for measuring optical density.

In the description above, a color or multi-channel densitometer is used to describe the invention. The invention is not limited to color densitometers, the invention may be used for single channel, or black and white densitometer as well.

What is claimed is:

1. A method, comprising:
   measuring a first optical density (OD) on a white area of a substrate;
   measuring a second OD on an area of the substrate printed with ink;
   determining a relative OD of the ink using the first OD and the second OD;
   determining an absolute OD of the ink by adding the relative OD of the ink to an absolute OD of the substrate; and
   controlling, by a printer, a printing process using the determined absolute OD of the ink.

2. The method of claim 1, wherein measuring the first OD is performed by a detector receiving light reflected from the white area and emitted by at least two different illumination sources that produce respective different colors of light, the detector detecting overlap of beams of light from the at least two different illumination sources.

3. The method of claim 1, wherein measuring the first OD and the second OD uses at least an orange illumination source, a green illumination source, and a blue illumination source.

4. The method of claim 1, wherein the substrate is selected from the group consisting of: a sheet of paper, a roll of paper, a sheet of cardboard, a piece of wood, a sheet of metal.

5. The method of claim 1, wherein the absolute OD of the ink measured at a first distance to the substrate printed with ink, and the absolute OD of the ink measured at a second, different distance to the substrate printed with ink, are essentially equal.

6. The method of claim 1, further comprising:
   measuring the absolute OD of the substrate using a color densitometer, wherein the absolute OD of the ink is determined using the measured absolute OD of the substrate.

7. The method of claim 1, further comprising:
   determining the absolute OD of the substrate using height sensitivities of illumination sources to the substrate.

8. An apparatus, comprising:
   at least one illumination source;
   illumination optics positioned to direct light from the at least one illumination source onto a target area;
   a detector positioned to collect light from the target area;
   detector optics positioned to focus light from the target area onto the detector;
   a controller coupled to the at least one illumination source and the detector and configured to:
      receive a measured first optical density (OD) when a white area of an object is in the target area, and receive a measured second OD when an area of the object printed with ink is in the target area,
      calculate a relative OD of the ink using the first measured OD and the second measured OD,
      calculate an absolute OD of the ink by adding the relative OD of the ink to an absolute OD of the object, and
      control a printing process using the calculated absolute OD of the ink.

9. The apparatus of claim 8, wherein the illumination optics direct the light from the at least one illumination source into the target area at a 45 degree angle.

10. The apparatus of claim 8, wherein the controller is to determine the absolute OD of the object by measuring the absolute OD of the object using a color densitometer.

11. The apparatus of claim 8, further comprising:
    a printer, wherein the target area is positioned in an output path of the printer and wherein the controller is to adjust the printer based at least in part by using the absolute OD of the ink.

12. The apparatus of claim 8, wherein the at least one illumination source comprises:
    an orange illumination source;
    a green illumination source; and
    a blue illumination source.

13. The apparatus of claim 8, wherein the at least one illumination source includes a plurality of illumination sources to produce respective different colors of light, wherein the detector is to detect overlap of beams of light from the plurality of illumination sources, and the first OD and the second OD are based on measurements of the detector resulting from the overlap of the beams of light from the plurality of illumination sources.

* * * * *